United States Patent
Katafuchi

(10) Patent No.: US 8,664,966 B2
(45) Date of Patent: Mar. 4, 2014

(54) DEVICE FOR EVALUATING DEGREE OF DEGRADATION OF LUBRICATING OIL

(75) Inventor: Tadashi Katafuchi, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 380 days.

(21) Appl. No.: 12/992,119

(22) PCT Filed: Mar. 3, 2009

(86) PCT No.: PCT/JP2009/053947
§ 371 (c)(1),
(2), (4) Date: Nov. 11, 2010

(87) PCT Pub. No.: WO2009/139211
PCT Pub. Date: Nov. 19, 2009

(65) Prior Publication Data
US 2011/0074452 A1 Mar. 31, 2011

(30) Foreign Application Priority Data
May 13, 2008 (JP) ................................ 2008-126314

(51) Int. Cl.
*G01R 27/08* (2006.01)
*G01N 33/26* (2006.01)

(52) U.S. Cl.
USPC ......................................... 324/698; 73/53.05

(58) Field of Classification Search
None
See application file for complete search history.

(56) References Cited

U.S. PATENT DOCUMENTS

| | | | | |
|---|---|---|---|---|
| 3,831,432 A | * | 8/1974 | Cox | 73/31.06 |
| 4,020,830 A | * | 5/1977 | Johnson et al. | 600/348 |
| 4,716,448 A | * | 12/1987 | Kelly | 257/253 |
| 4,773,970 A | * | 9/1988 | Purbrick et al. | 205/778.5 |
| 5,911,873 A | * | 6/1999 | McCarron et al. | 205/789 |
| 6,624,637 B1 | * | 9/2003 | Pechstein | 324/438 |

FOREIGN PATENT DOCUMENTS

| JP | 56-47614 A | 4/1981 |
|---|---|---|
| JP | 63-40855 A | 2/1988 |
| JP | 8-15219 A | 1/1996 |
| JP | 2003-114206 | 4/2003 |

OTHER PUBLICATIONS

Office Action issued Sep. 20, 2012, in Chineese patent Application No. 200980117759.5, filed May 13, 2008.
"pH electrode for Ion-Sensitive filed-effect transistor", contribution, "analytical instrument", forth quarter of 1995, p. 44-47.
International Search Report issued on Apr. 28, 2009 in corresponding International Application No. PCT/JP2009/053947 filed on Mar. 3, 2009.

(Continued)

*Primary Examiner* — Minh N Tang
(74) *Attorney, Agent, or Firm* — Oblon, Spivak, McClelland, Maier & Neustadt, L.L.P.

(57) ABSTRACT

A method of evaluation a degree of degradation of a lubricating oil, comprising: using a device for evaluating a degree of degradation of a lubricating oil, the device comprising a pH-ISFET which is free from a reference electrode; and measuring a current flowing between a drain and a source of the pH-ISFET with a first circuit wherein a constant voltage is applied between the drain and the source, or measuring a voltage between a drain and a source with a second circuit wherein a constant current is caused to flow between the drain and the source.

9 Claims, 3 Drawing Sheets

(56) References Cited

OTHER PUBLICATIONS

Kosuke Izutsu et al., "Use of pH-Sensitive ISFETs as Sensors for pH in Nonaqueous Solutions and for Proton Solvation", Chemistry Letters, Nov. 5, 1993, pp. 1843-1846.

Kosuke Izutsu et al., "Response of an Iridium Oxide pH-Sensor in Nonaqueous Solutions. Comparison with Other pH-Sensors", Analytical Sciences, Dec. 25, 1996, vol. 12, No. 6, pp. 905-909.

* cited by examiner

Measurement (a) and (b) are repeated and determine a state of degradation based on a difference between the measured values.

DEVICE FOR EVALUATING DEGREE OF DEGRADATION OF LUBRICATING OIL

TECHNICAL FIELD

The present invention relates to a device for evaluating a degree of degradation of a lubricating oil, a method of evaluating a degree of degradation of a lubricating oil, and an on-line lubricating oil management device.

BACKGROUND ART

A lubricating oil, in particular, an engine oil needs to be managed to be in a normal state because degradation thereof leads to decreases in operating efficiency, durability, etc. of such devices as an engine which use the oil.

For this reason, there is a demand for a device or a method which enables the degree of degradation to be measured in a simple manner, but there is no such device or method. Hence, such management has been performed that a time period of use is used as a measure of the degree of degradation, or a determination has been made as to the degree of degradation based on many property values acquired through analysis of the lubricating oil.

For example, there are proposed many methods in which the degree of degradation is evaluated by taking into account a dielectric constant and a time period of use of the lubricating oil, the degree of heavy use, etc. However, none of those methods provides measurement of the degree of degradation itself for the lubricating oil. Those methods are established based on the premise that there is no highly-reliable method for measurement of the degree of degradation. Those methods are low in reliability because results thereof are expected to vary considerably depending on the type and the use condition of the lubricating oil.

On the other hand, there is proposed a method in which, by assuming that degradation of the lubricating oil is represented by ionization change of an alkaline earth metal, in particular, calcium, contained in the lubricating oil, which is caused by the water content in the oil, an ISFET is employed to measure the degree of the ionization based on a potential difference between a reference electrode and the ISFET (see Patent Document 1). However, in a non-aqueous lubricating oil, metal ions are not able to exist in a stable manner, and hence it is impossible to perform accurate measurement for an oil with little water content.

[Patent Document 1] JP 63-40855 A

DISCLOSURE OF THE INVENTION

Problem to be Solved by the Invention

The present invention has an object to provide a device for evaluating a degree of degradation of a lubricating oil, a method of evaluating a degree of degradation of a lubricating oil, and an on-line lubricating oil management device, which overcome the above-mentioned drawback inherent in the related art so as to be able to measure the degree of degradation of the lubricating oil in a simple and stable manner.

Means for Solving the Problem

The inventors of the present invention have conducted an extensive research in order to solve the above-mentioned problem, and, as a result, have arrived at the present invention, focusing on the facts that an acidity of the lubricating oil indicates actual degradation of the lubricating oil and that the pH-ISFET is capable of measuring the acidity of a non-aqueous lubricating oil when used in an appropriate method. Specifically, the present invention provides:

[1] a device for evaluating a degree of degradation of a lubricating oil, including a pH-ISFET and a circuit for measuring a current flowing between a drain and a source of the pH-ISFET in a case where a constant voltage is applied between the drain and the source, or a circuit for measuring a voltage between the drain and the source in a case where a constant current is caused to flow between the drain and the source;

[2] the device for evaluating a degree of degradation of a lubricating oil according to the above [1], in which the pH-ISFET is free from a reference electrode;

[3] the device for evaluating a degree of degradation of a lubricating oil according to the above [1] or [2], in which the lubricating oil includes an engine oil;

[4] a method of evaluating a degree of degradation of a lubricating oil, including using the device for evaluating a degree of degradation of a lubricating oil according to any one of the above [1] to [3], and measuring an acidity of the lubricating oil by using, as an output, the current flowing between the drain and the source in the case where the constant voltage is applied between the drain and the source or the voltage between the drain and the source in the case where the constant current is caused to flow between the drain and the source;

[5] the method of evaluating a degree of degradation of a lubricating oil according to the above [4], further including providing a non-measurement time period by intermittently applying the constant voltage between the drain and the source or by causing the constant current to intermittently flow between the drain and the source;

the method of evaluating a degree of degradation of a lubricating oil according to the above [4] or [5], further including measuring, based on different voltage values or different current values, a current difference obtained between the drain and the source or a voltage difference obtained between the drain and the source by intermittently applying different voltages between the drain and the source or by causing different currents to intermittently flow between the drain and the source;

[7] the method of evaluating a degree of degradation of a lubricating oil according to any one of the above [4] to [6], in which the lubricating oil includes an engine oil; and

[8] an on-line lubricating oil management device, which uses the device for evaluating a degree of degradation of a lubricating oil according to any one of the above [1] to [3].

It should be noted that the pH-ISFET refers to an ion sensitive field effect transistor of hydrogen ion sensitive type.

Effects of the Invention

According to the present invention, there are provided the device and the method, which are capable of performing accurate measurement as to the state of degradation of the lubricating oil over a long period of time. Moreover, if a structure in which the reference electrode is not provided to the pH-ISFET is employed, the circuit of the device becomes further simpler, and the stability of the measured values is enhanced.

DESCRIPTION OF REFERENCE NUMERALS

Figure 1:
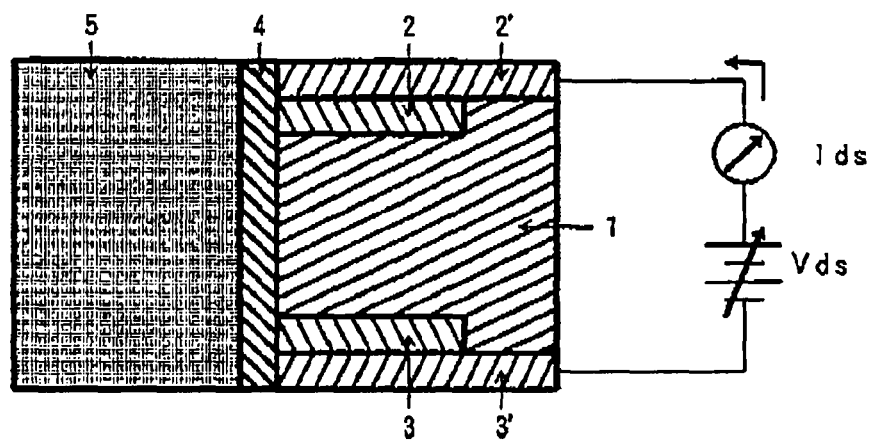
FIG. 1 A schematic diagram illustrating one example of a device for evaluating a degree of degradation of a lubricating oil according to the present invention.

1: p-type semiconductor
2: drain (n-type semiconductor)
2': drain electrode
3: source (n-type semiconductor)
3': source electrode
4: gate
5: lubricating oil
6: hydrogen ion permeable membrane
7: reference electrode

BEST MODE FOR CARRYING OUT THE INVENTION

As a pH-ISFET used in a device for evaluating a degree of degradation of a lubricating oil according to the present invention, a commonly-used ISFET of hydrogen ion sensitive type may be used.

The pH-ISFET is a commonly-used transistor in which two regions of n-type semiconductor (source and drain) are formed in a p-type substrate, and a gate formed of an insulating film is provided. As a gate material, there may be exemplified tantalum oxide ($Ta_2O_5$) and silicon nitride ($Si_3N_4$), for example.

Figure 2:
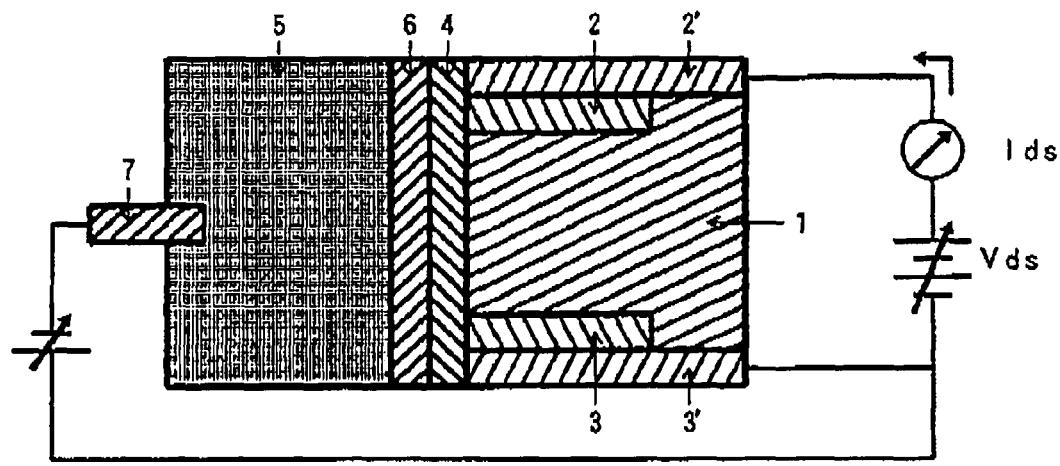
FIG. 2 A schematic diagram illustrating another example of the device for evaluating a degree of degradation of a lubricating oil according to the present invention.

FIG. 1 is a schematic diagram illustrating one example of the device for evaluating a degree of degradation of a lubricating oil according to the present invention, and FIG. 2 is a schematic diagram illustrating another example of the device for evaluating a degree of degradation of a lubricating oil according to the present invention. Hereinbelow, with reference to FIG. 1 and FIG. 2, description is given of the device for evaluating a degree of degradation of a lubricating oil and a method of evaluating a degree of degradation of a lubricating oil.

At both ends of a p-type semiconductor 1, there are formed two n-type semiconductor regions, that is, a drain 2 and a source 3, and wirings are connected to a drain electrode 2' and a source electrode 3', which are in contact with the respective regions. On one side of the p-type semiconductor 1 having the drain 2 and the source 3 formed therein, there is formed a gate 4, which has a surface thereof in contact with a lubricating oil 5.

When hydrogen ions of the lubricating oil 5 have accumulated around the gate 4, free holes, which are majority carriers of the p-type semiconductor, move away from the gate 4 due to repulsion. On the other hand, electrons existing as minority carriers in the p-type semiconductor are attracted to the gate 4, thereby forming an n-channel. As a result, a current flows between the drain 2 and the source 3.

Here, in the example of FIG. 2, a hydrogen ion permeable membrane 6 is provided, but the hydrogen ion permeable membrane 6 is not essential for the present invention because the principle is that the ISFET measures a potential of the gate.

As the concentration of the hydrogen ions in the lubricating oil 5 becomes higher, the n-channel becomes thicker, which causes a larger current to flow between the drain 2 and the source 3.

Accordingly, in a case where a voltage applied between the drain 2 and the source 3 (Vds) is kept constant, a current flowing between the drain 2 and the source 3 (Ids) becomes larger as the concentration of the hydrogen ions in the lubricating oil 5 becomes higher. On the other hand, in a case where the current caused to flow between the drain 2 and the source 3 (Ids) is kept constant, the voltage between the drain 2 and the source 3 (Vds) becomes smaller as the concentration of the hydrogen ions in the lubricating oil becomes higher.

By measuring such a current value that is obtained in the case where a constant voltage is applied or by measuring such a voltage value that is obtained in the case where a constant current is caused to flow, it becomes possible to make a determination as to the concentration of the hydrogen ions in the lubricating oil, that is, the degree of degradation. If such current value or voltage value is measured over a long period of time, the progress of degradation may be understood.

Like usual cases, the pH-ISFET may be provided with a reference electrode 7 for use, as illustrated in the example of FIG. 2. However, the pH-ISFET may be used without being provided with the reference electrode 7. This case is more preferred because the circuit is simpler and management of the reference electrode is not required.

It should be noted that, though not illustrated, the device for evaluating a degree of degradation of a lubricating oil is immersed into the lubricating oil in actual use so that the gate 4 (hydrogen ion permeable membrane 6 in the example of FIG. 2) is brought into contact with the lubricating oil 5, and thus needs to have a structure that allows such use. In addition, between the drain 2 and the source 3, there is connected a measurement circuit for measuring a current value in a case where a constant voltage is applied by a constant voltage device, or a measurement circuit for measuring a voltage value in a case where a constant current is caused to flow by a constant current device.

Immediately after measurement is started by applying a constant voltage or by causing a constant current to flow, the measured value does not become stable with a tendency of the current value Ids to increase gradually in the case where the constant voltage is applied or with a tendency of the voltage value Vds to decrease gradually in the case where the constant current is caused to flow. In both the cases, the measured value gradually settles into a constant value. Accordingly, a measurement time period is preferably set to 5 seconds or longer, particularly, 10 seconds or longer.

Further, if the measurement is performed only once, only the first output is measured, and the measured value tends to become unstable. Thus, it is preferred to provide non-measurement time period in which the constant voltage is not applied or the constant current is not caused to flow and to perform the measurement a plurality of times. Such conditions are preferred that allow the measured value to converge with the non-measurement time period set to 10 seconds or shorter and with the number of times the measurement is performed set to 5 times or more.

Figure 4:
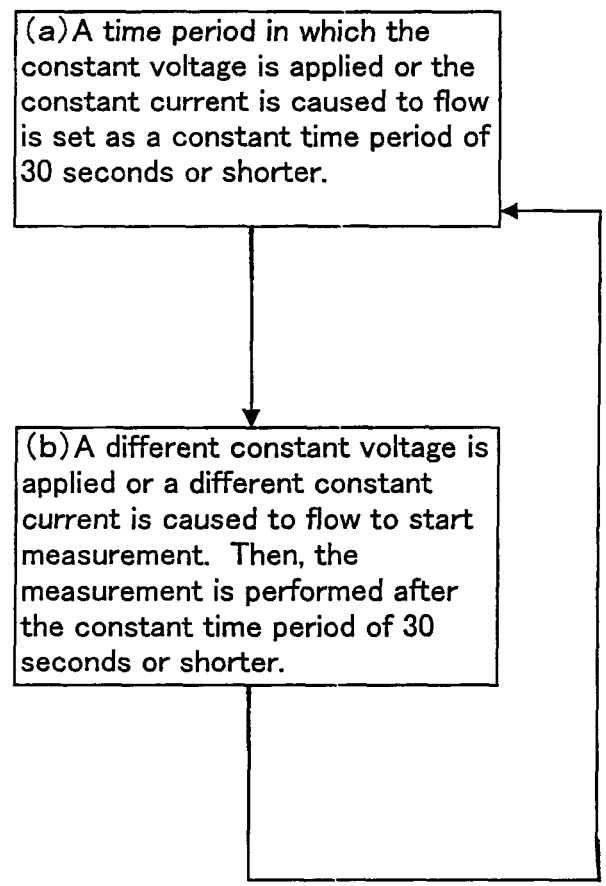
FIG. 4 A method flow showing measuring, based on different voltage values or different current values, a current difference obtained between the drain and the source or a voltage difference obtained between the drain and the source by intermittently applying different voltages between the drain and the source or by causing different currents to intermittently flow between the drain and the source.

There may be employed such a method that, by intermittently applying different voltages between the drain and the source or by causing different currents to intermittently flow between the drain and the source, a current difference obtained between the drain and the source or a voltage difference obtained between the drain and the source is measured based on different voltage values or different current values, as shown in FIG. 4. In this case, a time period in which the constant voltage is applied or the constant current is caused to flow is set as a constant time period of 30 seconds or shorter. A different constant voltage is applied or a different constant current is caused to flow to start measurement. Then, the measurement is performed after the constant time period of 30 seconds or shorter, which is repeated to determine a state of degradation based on a difference between the measured values.

The device for evaluating a degree of degradation of a lubricating oil according to the present invention may be incorporated as a part of, for example, an engine control unit system, so as to function as an on-line lubricating oil management device.

EXAMPLE

Detailed description is given below with reference to examples of the present invention, but the present invention is not limited to those examples.

Example 1

The detergency test method for lubricating oils for automotive diesel engines, JASO M 336-98, was carried out using a standard test oil, JASO DD6. The device as illustrated in FIG. 1 was used for the test oil, and a constant current of 0.5 mA was caused to flow between the drain 2 and the source 3 from start of the detergency test until a lapse of 200 hours, to thereby measure the voltage between the drain 2 and the source 3 (Vds) at constant time intervals. In the measurement, the non-measurement time period was set to 2 seconds, and the voltage was measured 18 seconds after the start of the measurement (after the constant current started to flow). Such measurement operation was repeated 10 times, and a convergence value of the measured voltage values was adopted as the voltage between the drain and the source (Vds) at that time point.

Figure 3:
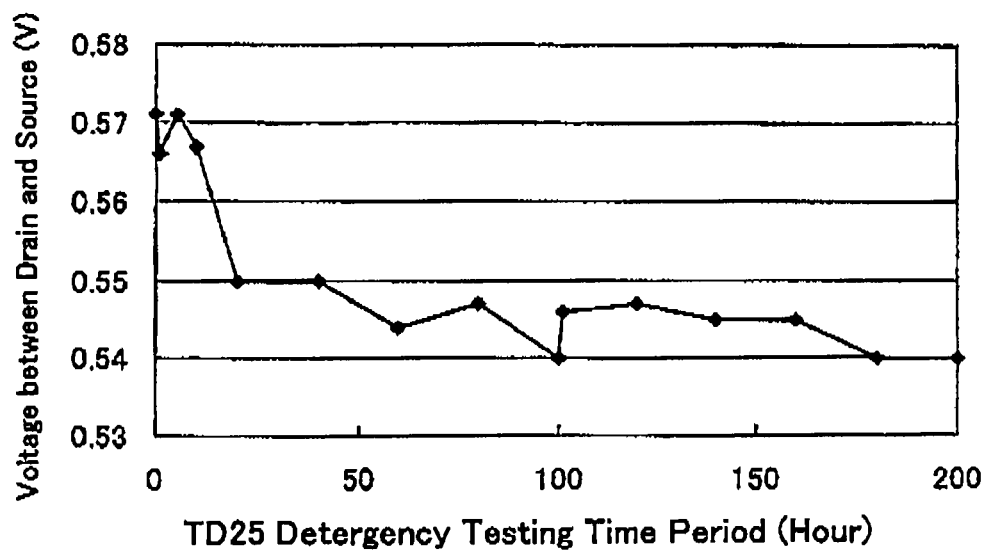
FIG. 3 A graph showing results obtained by measuring the degree of degradation of the lubricating oil with the use of the device for evaluating a degree of degradation of a lubricating oil according to the present invention.

FIG. 3 is obtained when results thereof are represented as a graph.

From the results, the following may be understood. When the engine testing time period becomes longer to cause the degradation of the lubricating oil to advance, the voltage between the drain and the source (Vds) decreases, meaning that the acidity is becoming higher. In addition, the values at 100 hours and 200 hours, at which the respective degrees of degradation of the oil are considered to be substantially equal, show substantially the same value.

INDUSTRIAL APPLICABILITY

According to the present invention, the device for evaluating a degree of degradation of a lubricating oil and the method therefor are capable of performing accurate measurement as to the state of degradation of the lubricating oil over a long period of time, and may be used as a remarkably useful device and method in the field of such devices as engines of various types that use lubricating oils.

The invention claimed is:

1. A method of evaluating a degree of degradation of a lubricating oil, comprising:
using a device for evaluating a degree of degradation of a lubricating oil, the lubricating oil being free from a reference electrode, the device comprising a pH-ISFET and a first circuit for measuring a current flowing between a drain and a source of the pH-ISFET in a case where a constant voltage is applied between the drain and the source, or a second circuit for measuring a voltage between the drain and the source in a case where a constant current is caused to flow between the drain and the source;
measuring the current flowing between the drain and the source of the pH-ISFET with the first circuit wherein the constant voltage is applied between the drain and the source, or measuring the voltage between the drain and the source with the second circuit wherein the constant current is caused to flow between the drain and the source by
providing a measurement time period and a non-measurement time period by intermittently applying the constant voltage between the drain and the source or by causing the current to intermittently flow between the drain and the source; and
evaluating the degradation of the lubricating oil based on the measured current or based on the measured voltage.

2. The method of evaluating a degree of degradation of a lubricating oil according to claim 1, further comprising measuring, based on different voltage values or different current values, a current difference obtained between the drain and the source or a voltage difference obtained between the drain and the source by intermittently applying different voltages between the drain and the source or by causing different currents to intermittently flow between the drain and the source.

3. The method of evaluating a degree of degradation of a lubricating oil according to claim 1, wherein the lubricating oil comprises an engine oil.

4. The method of evaluating a degree of degradation of a lubricating oil according to claim 1, wherein the measurement time period is set to 5 seconds or longer.

5. The method of evaluating a degree of degradation of a lubricating oil according to claim 1, wherein the non-measurement time period is set to 10 seconds or shorter.

6. The method of evaluating a degree of degradation of a lubricating oil according to claim 1, wherein a number of times the measuring is performed is set to 5 times or more.

7. A lubricating oil management apparatus, comprising:
a device for evaluating a degree of degradation of a lubricating oil, the lubricating oil being free from a reference electrode, the device being incorporated as a part of an engine control unit system, wherein
the device comprises a pH-ISFET and a circuit for measuring a current flowing between a drain and a source of the pH-ISFET in a case where a constant voltage is applied between the drain and the source, or a circuit for measuring a voltage between the drain and the source in a case where a constant current is caused to flow between the drain and the source,
the device provides a measurement time period and a non-measurement time period by intermittently applying the constant voltage between the drain and the source or by causing the current to intermittently flow between the drain and the source, and
the device evaluates the degradation of the lubricating oil based on the measured current or based on the measured voltage.

8. A method of evaluating a degree of degradation of a lubricating oil, comprising:
using a device for evaluating a degree of degradation of a lubricating oil, the lubricating oil being free from a reference electrode, the device comprising a pH-ISFET and a first circuit for measuring a current flowing between a drain and a source of the pH-ISFET in a case where a constant voltage is applied between the drain and the source, or a second circuit for measuring a voltage between the drain and the source in a case where a constant current is caused to flow between the drain and the source;

measuring the current flowing between the drain and the source of the pH-ISFET with the first circuit wherein the constant voltage is applied between the drain and the source, or measuring the voltage between the drain and the source with the second circuit wherein the constant current is caused to flow between the drain and the source by measuring, based on different voltage values or different current values, a current difference obtained between the drain and the source or a voltage difference obtained between the drain and the source by intermittently applying different voltages between the drain and the source or by causing different currents to intermittently flow between the drain and the source; and evaluating the degradation of the lubricating oil based on the measured current or based on the measured voltage.

9. A lubricating oil management apparatus, comprising:

a device for evaluating a degree of degradation of a lubricating oil, the lubricating oil being free from a reference electrode, the device being incorporated as a part of an engine control unit system, wherein the device comprises a pH-ISFET and a circuit for measuring a current flowing between a drain and a source of the pH-ISFET in a case where a constant voltage is applied between the drain and the source, or a circuit for measuring a voltage between the drain and the source in a case where a constant current is caused to flow between the drain and the source, the device measures, based on different voltage values or different current values, a current difference obtained between the drain and the source or a voltage difference obtained between the drain and the source by intermittently applying different voltages between the drain and the source or by causing different currents to intermittently flow between the drain and the source, and the device evaluates the degradation of the lubricating oil based on the measured current or based on the measured voltage.

* * * * *